(12) United States Patent
Majano

(10) Patent No.: US 9,387,102 B2
(45) Date of Patent: Jul. 12, 2016

(54) SHEATHLESS PREDILATATION ANGIOPLASTY AND STENT DEPLOYMENT CATHETER

(71) Applicant: Romeo Majano, Coral Gables, FL (US)

(72) Inventor: Romeo Majano, Coral Gables, FL (US)

(73) Assignee: Clever Cath Technologies, LLC, Coral Gables, FL (US)

(*) Notice: Subject to any disclaimer, the term of this patent is extended or adjusted under 35 U.S.C. 154(b) by 0 days.

(21) Appl. No.: 14/226,861

(22) Filed: Mar. 27, 2014

(65) Prior Publication Data

US 2015/0272757 A1    Oct. 1, 2015

(51) Int. Cl.
*A61F 2/958*    (2013.01)
*A61M 25/10*    (2013.01)

(52) U.S. Cl.
CPC .......... *A61F 2/958* (2013.01); *A61F 2250/0098* (2013.01); *A61M 25/104* (2013.01); *A61M 25/1011* (2013.01)

(58) Field of Classification Search
CPC ............... A61M 25/1011; A61F 2/958; A61F 2250/0098
USPC .................................. 623/1.11, 1.12; 606/200
See application file for complete search history.

(56) References Cited

U.S. PATENT DOCUMENTS

| | | | |
|---|---|---|---|
| 4,955,895 A | 9/1990 | Sugiyama et al. | |
| 5,117,831 A | 6/1992 | Jang et al. | |
| 5,192,297 A | 3/1993 | Hull | |
| 5,201,315 A | 4/1993 | Griffith | |
| 5,226,889 A | 7/1993 | Sheiban | |
| 5,456,694 A | 10/1995 | Marin et al. | |
| 5,639,274 A | 6/1997 | Fischell | |
| 5,725,535 A | 3/1998 | Hegde et al. | |
| 5,743,874 A | 4/1998 | Fischell et al. | |
| 6,074,362 A | 6/2000 | Jang et al. | |
| 6,585,657 B2 | 7/2003 | Yock | |
| 2004/0267239 A1 | 12/2004 | Jang | |
| 2005/0027247 A1* | 2/2005 | Carrison et al. | 604/101.01 |
| 2007/0078505 A1* | 4/2007 | Dimitrov | A61F 2/958 623/1.11 |
| 2008/0188803 A1 | 8/2008 | Jang | |
| 2010/0222861 A1* | 9/2010 | Dibie | 623/1.11 |
| 2010/0305678 A1 | 12/2010 | Alaswad | |

OTHER PUBLICATIONS

Wholey, MH, "A newly designed angioplasty catheter: 'the Gemini balloon'", Abstract only. Cardiovasc Intervent Radiol., 1998; 11(1):42-4.

(Continued)

*Primary Examiner* — Darwin Erezo
*Assistant Examiner* — Anh Dang
(74) *Attorney, Agent, or Firm* — Joseph E. Maenner; Maenner & Associates, LLC

(57) ABSTRACT

A coronary predilatation and stent deployment catheter assembly includes a sheathless unitary catheter body having a proximal end and a distal end. A predilatation balloon is located at the distal end of the body. A stent inflation balloon is located along the body proximally of the predilatation balloon and an expandable stent is disposed over the stent inflation balloon. A predilatation balloon inflation connection is located proximally of the stent inflation balloon and in fluid communication with the predilatation balloon and a stent balloon inflation connection is located proximally of the stent inflation balloon and in fluid communication with the stent inflation balloon. A method of operating the catheter assembly is also disclosed.

9 Claims, 5 Drawing Sheets

(56) References Cited

OTHER PUBLICATIONS

Turi, Z. G., et al. "Preservation of distal coronary perfusion during prolonged belloon inflation with an autoperfusion angioplasty catheter." Journal of the American Heart Association, 1987; 75, pp. 1273-1280.

Topol, Eric J., et al., "Selection of Dilatation Hardware for PTCA-1085", Catheterization and Cardiovascular Disgnosis 11:, pp. 629-637, 1985.

* cited by examiner

SHEATHLESS PREDILATATION ANGIOPLASTY AND STENT DEPLOYMENT CATHETER

FIELD OF THE INVENTION

The present invention relates to a unitary catheter assembly that is used to predilate a blockage within a coronary artery and to deploy a stent across the blockage.

BACKGROUND OF THE INVENTION

Percutaneous coronary intervention ("PCI"), or "angioplasty", is an invasive procedure that is used to open a blockage in a coronary artery, that is, an artery that provides blood to the heart. In a PCI procedure, a cardiologist inserts a catheter into an artery in the upper arm or thigh of a patient and guides the catheter through the arteries to the affected coronary artery. With the catheter in place, the doctor threads a guide wire across the blockage. After the wire is across the blockage and positioned distal to the blockage, the cardiologist then advances the catheter with a deflated balloon. The balloon is inflated to dilate the blockage to make enough room for the insertion of a second catheter with its own balloon and stent. After dilating the blockage, the balloon is deflated and the first catheter is removed proximally.

At this point in the procedure, complications can occur. For example, coronary dissections or ruptures in the wall of the artery can occur and shut down blood flow. If the guide wire, which is in position across the blockage, is lost or pulled back proximal of the blockage during the first catheter exchange, such an occurrence can result in a heart attack if rewiring the artery is not possible after breakage of the wall.

Assuming that such complications do not occur, the second catheter with another balloon and a stent or metal mesh surrounding the balloon is advanced distally along the guide wire to the area of the blockage. The second balloon is inflated, which expands the stent and completely opens the blockage. The second balloon is then deflated, leaving the stent in place, and the second catheter is then removed.

U.S. Pat. No. 5,226,889 to Sheiban ("Sheiban") discloses a double balloon catheter for stent implantation. This catheter, however, has several drawbacks. Sheiban's proximal balloon and the distal balloon are only separated from each other by a small radiopaque marker. A drawback to this configuration is that visualization of the predilated angioplasty area is difficult to confirm. Further, the proximity of the distal balloon to the proximal balloon in Sheiban's catheter restricts the "pushability" of the catheter through narrow, tortuous, and sometimes occluded vessels. Without a significant separation between the two balloons, the interventionalist may have an extraordinarily difficult time advancing the catheter without causing trauma to the vessel walls.

An improved device for performing the above procedure without requiring the insertion and removal of two separate catheters is required.

BRIEF SUMMARY OF THE INVENTION

Briefly, the present invention provides a coronary predilatation and stent deployment catheter assembly that includes a sheathless unitary catheter body having a proximal end and a distal end and a predilatation balloon located at the distal end of the body. A stent inflation balloon is located along the body proximally of the predilatation balloon and an expandable stent is disposed over the stent balloon. A predilatation balloon inflation connection is located proximally of the stent inflation balloon and in fluid communication with the predilatation balloon and a stent balloon inflation connection is located proximally of the stent inflation balloon and in fluid communication with the stent inflation balloon.

Further, the present invention provides a method of performing an angioplasty procedure comprising the steps of inserting a single unsheathed catheter assembly into a blood vessel such that a first balloon is located within a blockage in the blood vessel; inflating the first balloon to at least partially open the blockage in the blood vessel; contracting the first balloon; advancing the catheter distally until a second balloon having an expandable stent mounted thereon is located within the blockage; expanding the second balloon and the stent, thereby further opening the blockage; contracting the second balloon and leaving the stent within the blood vessel; and removing the single catheter assembly proximally from the blood vessel.

Additionally, the present invention provides a sheathless catheter assembly comprising a unitary catheter body having a proximal end and a distal end. A first balloon is located proximally of the distal end. A second balloon is located proximally of the first balloon. A balloon-expandable stent is disposed over the second balloon.

BRIEF DESCRIPTION OF THE DRAWINGS

The accompanying drawings, which are incorporated herein and constitute part of this specification, illustrate the presently preferred embodiments of the invention, and, together with the general description given above and the detailed description given below, serve to explain the features of the invention. In the drawings.

DETAILED DESCRIPTION OF THE INVENTION

Figure 1:
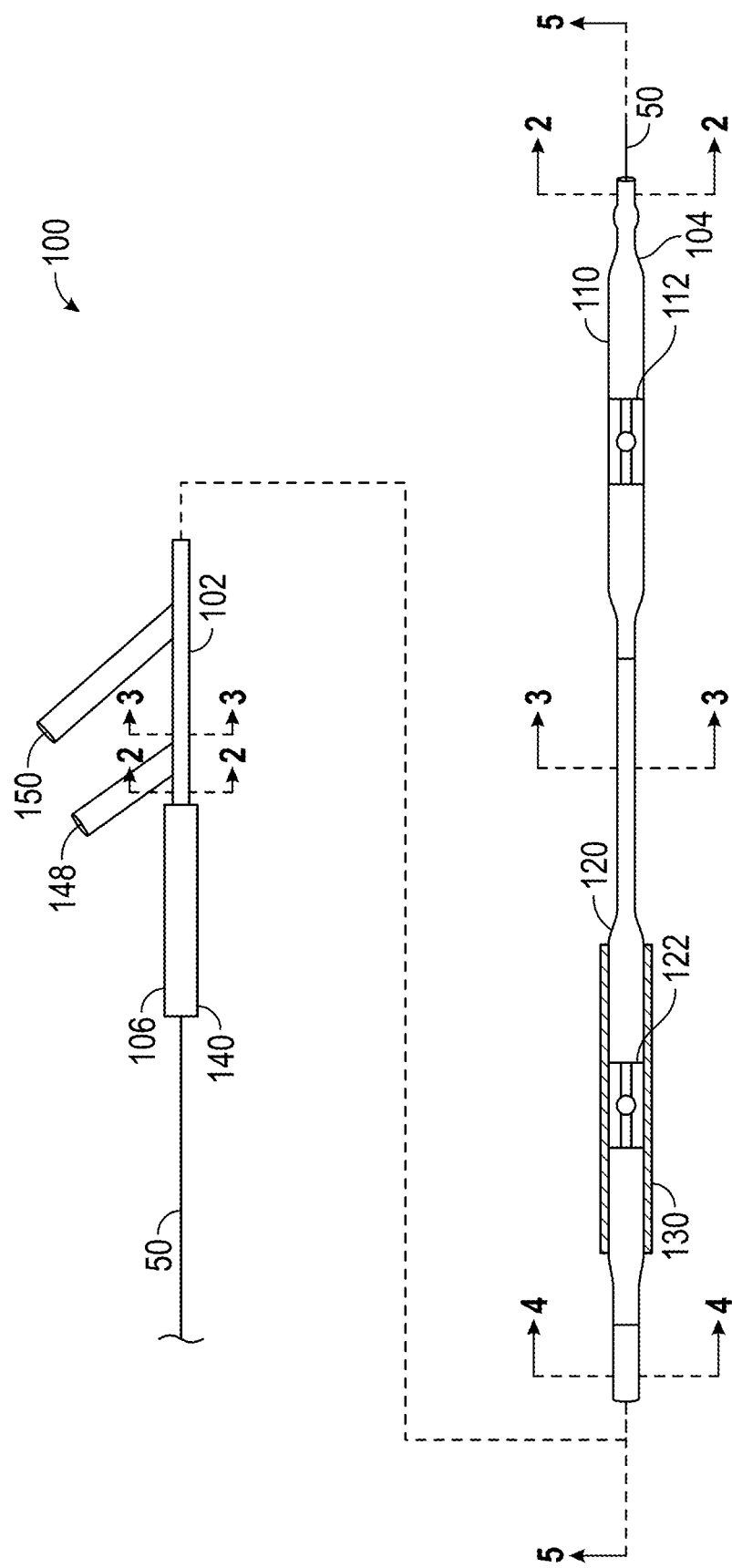
FIG. 1 is a side elevational view of a sheathless catheter assembly according to a first embodiment of the present invention.

In the drawings, like numerals indicate like elements throughout. Certain terminology is used herein for convenience only and is not to be taken as a limitation on the present invention. The terminology includes the words specifically mentioned, derivatives thereof and words of similar import. As used herein, the term "fluid" can mean and material that flows, including a liquid or a gas. The term "proximal" defines a location closer to the inserting physician and the term "distal" defines a location farther from the inserting physician. The embodiments illustrated below are not intended to be exhaustive or to limit the invention to the precise form disclosed. These embodiments are chosen and described to best explain the principle of the invention and its application and practical use and to enable others skilled in the art to best utilize the invention.

Reference herein to "one embodiment" or "an embodiment" means that a particular feature, structure, or characteristic described in connection with the embodiment can be included in at least one embodiment of the invention. The appearances of the phrase "in one embodiment" in various places in the specification are not necessarily all referring to the same embodiment, nor are separate or alternative embodiments necessarily mutually exclusive of other embodiments. The same applies to the term "implementation."

As used in this application, the word "exemplary" is used herein to mean serving as an example, instance, or illustration. Any aspect or design described herein as "exemplary" is not necessarily to be construed as preferred or advantageous over other aspects or designs. Rather, use of the word exemplary is intended to present concepts in a concrete fashion.

Additionally, the term "or" is intended to mean an inclusive "or" rather than an exclusive "or". That is, unless specified otherwise, or clear from context, "X employs A or B" is intended to mean any of the natural inclusive permutations. That is, if X employs A; X employs B; or X employs both A and B, then "X employs A or B" is satisfied under any of the foregoing instances. In addition, the articles "a" and "an" as used in this application and the appended claims should generally be construed to mean "one or more" unless specified otherwise or clear from context to be directed to a singular form.

Referring to FIGS. 1-5, a first exemplary embodiment of a catheter assembly 100 according to the present invention is shown. Catheter assembly 100 is used to open up blockages within coronary arteries.

Catheter assembly 100 is specifically designed for use within narrow coronary arteries that have an inside diameter of typically 6 French or less. The fact that catheter assembly 100 is sheathless allows catheter assembly 100 to be inserted into such narrow arteries. Sheathed catheters are too wide in diameter to fit into these arteries, given the additional width of the sheath itself.

Catheter assembly 100 has a unitary catheter body 102 that incorporates a predilatation balloon 110 at a distal end 104 of body 102 and a combination stent balloon 120 and stent 130 are located proximally of predilatation balloon 110. In an exemplary embodiment, predilatation balloon 110 has a deflated diameter of about 2.5 millimeters and a length of about 15 millimeters. Also, stent balloon 110 can include a radiopaque marker 112 disposed on an exterior thereof to allow for imaging and locating stent balloon 110 within a blood vessel 52 (shown in FIG. 8) during an angioplasty procedure.

In an exemplary embodiment, stent balloon 120 and stent 130 are located between about 10 millimeters and about 15 millimeters proximally from predilatation balloon 110. In an exemplary embodiment, catheter body 102 can be constructed from polytetrafluoroethylene, although those skilled in the art will recognize that catheter body 102 can be constructed from other material. Further, each of predilatation balloon 110 and stent balloon 120 inflate upon introduction of an inflation fluid therein, and contract toward their original size upon release or withdrawal of the inflation fluid from inside each of predilatation balloon 110 and stent balloon 120.

Figure 2:
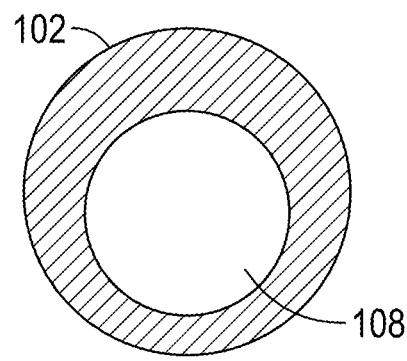
FIG. 2 is a sectional view of the sheathless catheter assembly of FIG. 1, taken along lines 2-2 of FIG. 1.

Catheter assembly 100 also includes a proximal end 106. As shown in FIG. 2, catheter assembly 100 includes a guide wire lumen 108 that extends from proximal end 106, through catheter body 102, to distal end 104. Guide wire lumen 108 is sized to allow a guide wire 50 to extend fully therethrough between proximal end 102 and distal end 104.

Figure 3:
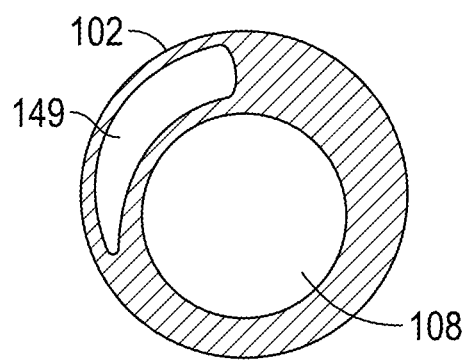
FIG. 3 is a sectional view of the sheathless catheter assembly of FIG. 1, taken along lines 3-3 of FIG. 1.
Figure 5:
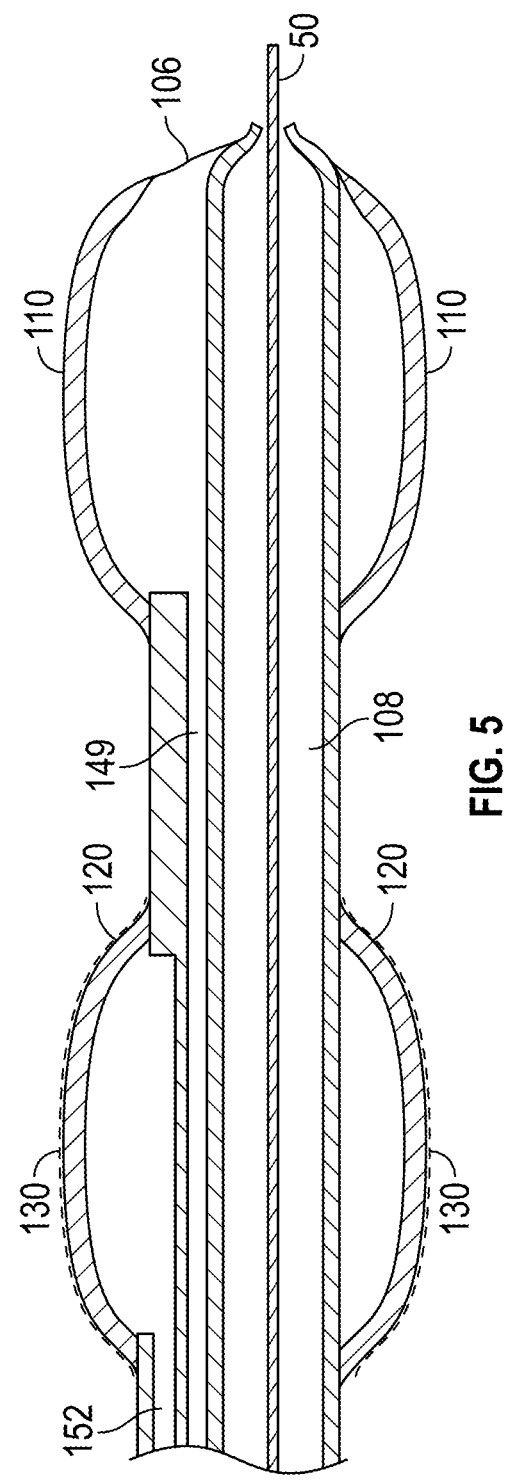
FIG. 5 is a sectional view of the sheathless catheter assembly of FIG. 1, taken along lines 5-5 of FIG. 1.

A predilatation balloon inflation connection 148 is located distally of proximal end 106. Predilatation balloon inflation connection 148 is releasably connectable to an inflation source (not shown) that provides an inflation fluid such as, for example, saline, to inflate predilatation balloon 110. As shown in FIGS. 3 and 5, a predilatation inflation lumen 149 provides fluid communication between predilatation balloon inflation connection 148 and predilatation balloon 110. Predilatation inflation lumen 149 extends through stent balloon 120.

A stent balloon inflation connection 150 is located distally of predilatation balloon inflation connection 148. While stent balloon inflation connection 150 is shown as being located distally of predilatation balloon inflation connection 148, those skilled in the art will recognize that stent balloon inflation connection 150 can be located proximally of predilatation balloon inflation connection 148 without departing from the scope of the present invention.

Figure 4:
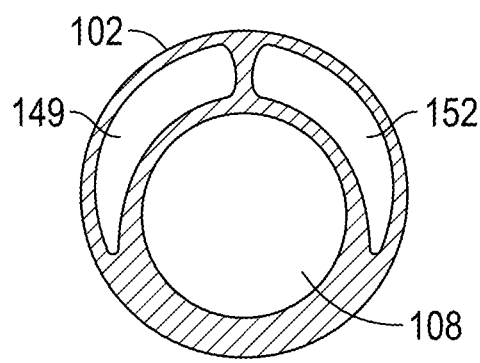
FIG. 4 is a sectional view of the sheathless catheter assembly of FIG. 1, taken along lines 4-4 of FIG. 1.

Stent balloon inflation connection 150 is releasably connectable to an inflation source (not shown) that provides an inflation fluid such as, for example, saline, to inflate stent balloon 120. The same fluid source that is used to inflate predilatation balloon 110 can be used to inflate stent balloon 120. As shown in FIGS. 4 and 5, a stent balloon inflation lumen 152 provides fluid communication between stent balloon inflation connection 150 and stent balloon 120. Referring back to FIG. 1, stent balloon 120 includes at least one radiopaque marker 122 that allows the treating physician to locate stent balloon 120 within blood vessel 52.

Stent 130 is an expandable stent as is well known in the art. Stent 130 is not self-expanding, but is expanded by the inflation of stent balloon 120. Stent 130 remains expanded after stent balloon 120 is deflated. Further, in an exemplary embodiment, stent 130 has an expanded size of customarily known, industry standard, and well-known coronary stents have unexpanded diameters within typical ranges of between about 2.5 millimeters and about 4 millimeters in diameter and between about 12 millimeters and about 33 millimeters in length. Additionally, in an exemplary embodiment, stent 130 does not include a graft, although those skilled in the art will recognize that a graft may be utilized with stent 130.

Figure 6:
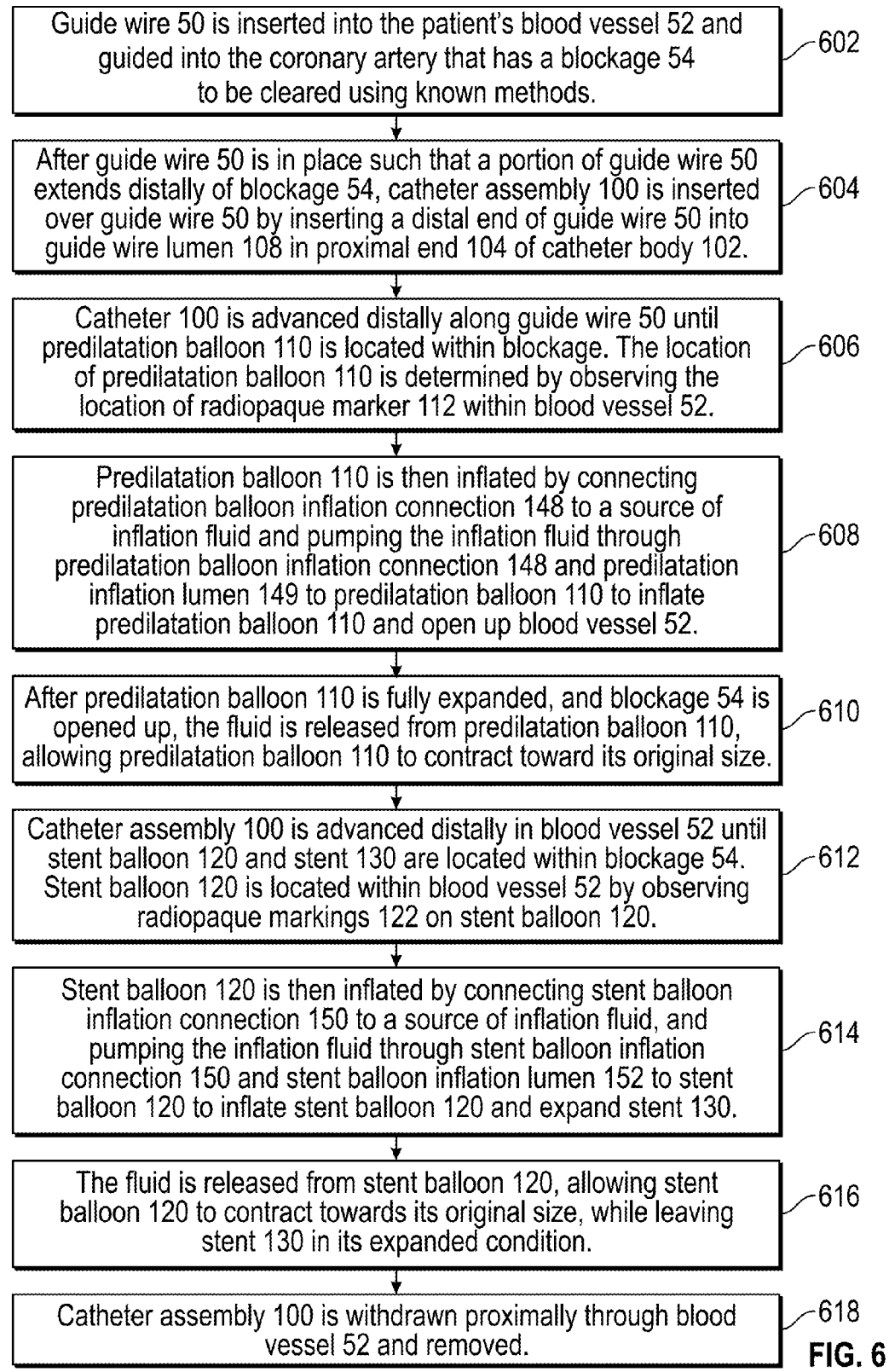
FIG. 6 is a flow chart illustration an exemplary operation of the sheathless catheter assembly of FIG. 1.
Figure 7:
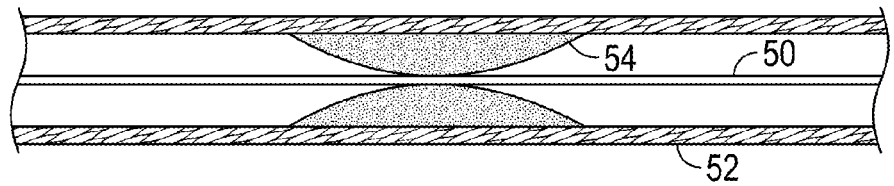
FIG. 7 is a side elevational view, in section, of a coronary artery showing a guide wire being passed through a blockage in the artery.

To use catheter assembly 100, and as explained in flowchart 600 of FIG. 6, in step 602, guide wire 50 is inserted into the patient's blood vessel 52, such as, for example, through a femoral artery, and guided into the coronary artery that has a blockage 54 to be cleared using known methods, as shown in FIG. 7. After guide wire 50 is in place such that a portion of guide wire 50 extends distally of blockage 54, in step 604, catheter assembly 100 is inserted over guide wire 50 by inserting a distal end of guide wire 50 into guide wire lumen 108 in proximal end 104 of catheter body 102.

Figure 8:
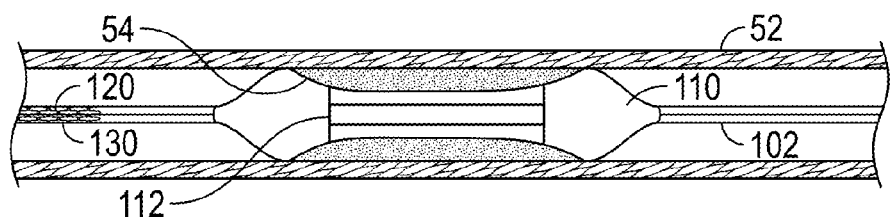
FIG. 8 is a side elevational view, in section, of the coronary artery of FIG. 8, with a predilatation balloon of the sheathless catheter assembly of FIG. 1 inflated at the site of the blockage.

In step 606, catheter 100 is advanced distally along guide wire 50 until predilatation balloon 110 is located within blockage 54, as shown in FIG. 8. The location of predilatation balloon 110 is determined by observing the location of radiopaque marker 112 within blood vessel 52 using known techniques. Predilatation balloon 110 is then inflated in step 608 by connecting predilatation balloon inflation connection 148 to a source of inflation fluid (not shown), and pumping the inflation fluid through predilatation balloon inflation connection 148 and predilatation inflation lumen 149 to predilatation balloon 110 to inflate predilatation balloon 110 and open up blood vessel 52, as shown in FIG. 8.

After predilatation balloon 110 is fully expanded, and blockage 54 is opened up, in step 610, the fluid is released from predilatation balloon 110, allowing predilatation balloon 110 to contract toward its original size. In step 612, catheter assembly 100 is advanced distally in blood vessel 52 until stent balloon 120 and stent 130 are located within blockage 54. Stent balloon 120 is located within blood vessel 52 by observing radiopaque markings 122 on stent balloon 120.

Figure 9:
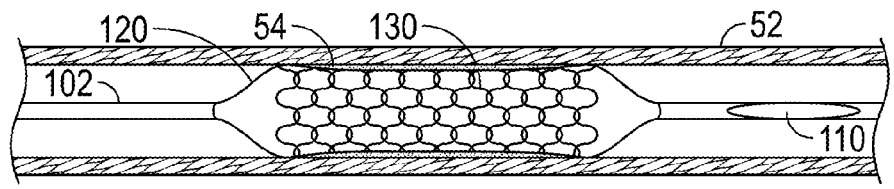
FIG. 9 is a side elevational view, in section, of the coronary artery of FIG. 8, with a stent inflation balloon of the sheathless catheter assembly of FIG. 1 inflated to expand a stent at the site of the blockage.

In step 614, stent balloon 120 is then inflated by connecting stent balloon inflation connection 150 to a source of inflation fluid (not shown), and pumping the inflation fluid through stent balloon inflation connection 150 and stent balloon inflation lumen 152 to stent balloon 120 to inflate stent balloon 120 and expand stent 130, as shown in FIG. 9. In step 616, the fluid is released from stent balloon 120, allowing stent balloon 120 to contract toward its original size, while leaving stent 130 in its expanded condition. In step 618, catheter assembly 100 is withdrawn proximally through blood vessel 52 and removed.

The inventive catheter assembly and method of the present invention obviates the need for two or more catheters, along with several catheter exchanges or manipulations to perform the method. This in turn decreases the chance of losing the position of the guide wire during the catheter balloon extraction. Further, increased pushability and turgor of the inventive assembly may improve the ease of advancing the catheter through calcific and tortuous arteries, especially when part of the inventive catheter assembly is already distally past the blockage.

Additionally, the lower cost of a single catheter, along with less time required for catheter laboratory (Cath Lab) personnel may significantly decrease the cost of an angioplasty procedure.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

What is claimed is:

1. A coronary predilatation and stent deployment catheter assembly consisting of:
   a single sheathless unitary catheter body having a proximal end and a distal end, wherein the catheter body has a lumen extending between the proximal end and the distal end;
   a predilatation balloon located at the distal end of the body;
   a stent inflation balloon located along the body a distance of between about 10 millimeters and about 15 millimeters proximally of the predilatation balloon;
   an expandable stent disposed over the stent balloon;
   a predilatation balloon inflation connection located proximally of the stent inflation balloon and in fluid communication with the predilatation balloon through a predilatation inflation lumen;
   a stent balloon inflation connection located proximally of the stent inflation balloon and in fluid communication with the stent inflation balloon through a stent balloon inflation lumen;
   a radiopaque marker disposed on the predilatation balloon; and
   a radiopaque marker disposed on the stent inflation balloon.

2. The coronary predilatation and stent deployment catheter assembly according to claim 1, wherein the predilatation balloon inflation connection is located proximally of the stent balloon inflation connection.

3. The coronary predilatation and stent deployment catheter assembly according to claim 1, wherein the stent is a balloon-expandable stent.

4. A sheathless catheter assembly consisting of:
   a. a single unitary catheter body having a proximal end and a distal end, and a guide wire lumen extending therethrough;
   b. a guide wire extending through the guide wire lumen;
   c. a first balloon located proximally of the distal end;
   d. a second balloon located a distance of between about 10 millimeters and about 15 millimeters proximally of the first balloon;
   e. a balloon-expandable stent disposed over the second balloon;
   f. a first balloon inflation connection located proximally of the second balloon and in fluid communication with the first balloon though a first inflation lumen;
   g. a second balloon inflation connection located proximally of the second balloon and in fluid communication with the second balloon through a second inflation lumen;
   h. a radiopaque marker disposed on the first balloon; and
   i. a radiopaque marker disposed on the second balloon.

5. The sheathless catheter assembly according to claim 4, wherein the body is sized for insertion into a vessel having a diameter of about 6 French.

6. A coronary predilatation and stent deployment catheter assembly consisting of:
   a single sheathless unitary catheter body having a proximal end and a distal end and a guide wire lumen extending therethrough;
   a guide wire extending through the guide wire lumen;
   a predilatation balloon located at the distal end of the body;
   a predilatation balloon connection located proximally of the predilatation balloon;
   a predilatation inflation lumen providing fluid communication between the predilatation balloon and the predilatation balloon connection;
   a radiopaque marker disposed on the predilatation balloon;
   a stent balloon located along the body proximally of the predilatation balloon;
   a stent balloon inflation connection located proximally of the stent balloon;
   a stent balloon inflation lumen providing fluid communication between the stent balloon and the stent balloon inflation connection;
   a radiopaque marker disposed on the stent balloon;
   an expandable stent disposed over the balloon.

7. The coronary predilatation and stent deployment catheter assembly according to claim 6, wherein the catheter body is sized for insertion into a vessel having a diameter of about 6 French.

8. The coronary predilatation and stent deployment catheter assembly according to claim 6, wherein between about 10 millimeters and about 15 millimeters of the catheter body extends between the predilatation balloon and the stent balloon.

9. The coronary predilatation and stent deployment catheter assembly according to claim 8, wherein the between about 10 millimeters and about 15 millimeters of the catheter body is free from radiopaque markings.

* * * * *